United States Patent [19]
Shikakubo et al.

[11] Patent Number: 6,012,603
[45] Date of Patent: Jan. 11, 2000

[54] NEEDLE SUPPLY DEVICE

[75] Inventors: Kenji Shikakubo, Sakaimachi; Takahiro Itoh, Miyashiromachi; Gennai Yanagisawa, Matsumoto, all of Japan

[73] Assignee: Kabushiki Kaisha Azwell (Azwell Inc.), Osaka-fu, Japan

[21] Appl. No.: 08/930,447

[22] PCT Filed: Jan. 28, 1997

[86] PCT No.: PCT/JP97/00184
    § 371 Date: Sep. 29, 1997
    § 102(e) Date: Sep. 29, 1997

[87] PCT Pub. No.: WO97/27805
    PCT Pub. Date: Aug. 7, 1997

[30] Foreign Application Priority Data

Jan. 30, 1996 [JP] Japan .................................. 8-014578

[51] Int. Cl.[7] .................................................. B65H 3/60
[52] U.S. Cl. .......................................... 221/203; 221/277
[58] Field of Search ..................................... 221/277, 200, 221/203, 202, 258; 198/391, 396, 389, 345.1, 468.6

[56] References Cited

U.S. PATENT DOCUMENTS

| 4,922,904 | 5/1990 | Uetake et al. | 606/226 |
| 5,191,960 | 3/1993 | Waveham | 198/391 |
| 5,394,971 | 3/1995 | Colligan et al. | 198/391 |
| 5,511,670 | 4/1996 | Demarest et al. | 209/540 |

*Primary Examiner*—Kenneth W. Noland
*Attorney, Agent, or Firm*—Jordan and Hamburg, LLP

[57] ABSTRACT

This invention relates to a needle supply device for use in a needle attached suture manufacturing apparatus or its equivalent to automatically supply curved needles one by one to a predetermined position of the apparatus in a state that the needle is accurately set in the same posture. The needle supply device has a passage defining member 32 including a needle storage portion 42, passages 44 and 46, and a needle discharge tray 55 in this order. By driving the passage defining member 32 to vibrate, needles N set on the needle storage portion 42 proceed along the passages 44 and 46 toward the needle discharge tray 55. There are provided selecting units 48, 50, and 52 each in a certain passage form on the way of the passages 44 and 46 to exclusively allow the needles N in the predetermined posture to pass while maintaining the predetermined posture.

20 Claims, 13 Drawing Sheets

NEEDLE SUPPLY DEVICE

BACKGROUND ART

This invention relates to a needle supply device for accommodating such as curved needles for surgical operations and the like, and for supplying the needles to a predetermined position of an apparatus for manufacturing sutures attached with the needles.

Recently, in the field of medical industry, there have been marketed sterilized needle-attached sutures (sutures attached with needles) for surgical operations in which the point of a suture is fixedly attached to a needle. There have also been known apparatuses for manufacturing such needle-attached sutures comprising a needle retaining unit for retaining a needle in a certain posture (or direction), a suture inserting unit for inserting a suture into an insertion hole of the end of the needle in the certain fixed posture, and a swaging die for fixedly swaging the end of the needle with the suture inserted in the insertion hole to produce a needle-attached suture.

The prior art mentioned above has been involved with the following problems to overcome.

Generally, such a needle for surgical operations and the like is curved into a substantially arc shape, and thus it has a certain directionality. Accordingly, in producing needle-attached sutures by the above manufacturing apparatus, the needles are required to be supplied to the needle retaining unit one by one in a state that they are set accurately in the same direction. However, a device for automatically supplying needles in the same posture has not ever been developed, and it has been inevitable that the needle supply relies on manual operations.

In view of the above, an object of this invention is to provide a needle supply device for use in a needle-attached suture manufacturing apparatus and the like capable of supplying curved needles, which are at randomly set with its direction being irregular, to a predetermined position of the apparatus one by one in a state that all the needles are oriented in the same direction accurately.

DISCLOSURE OF THE INVENTION

To solve the above problems, this invention has adopted the following arrangement.

This invention is directed to a needle supply device for accommodating curved needles and for supplying the needles in a certain posture to a predetermined position one by one, the needle supply device comprises: a passage defining member including a needle storage portion in which the needles are accommodated, a needle discharge portion, and a needle path connecting the needle storage portion and the needle discharge portion; needle conveyor means for forwarding the needle in the needle storage portion along the needle path to the needle discharge portion by vibrating the passage defining member; and select means in a passage form for exclusively allowing the needle in the posture meeting a predetermined condition to pass while maintaining the posture.

In the needle supply device, the needles are set in the needle storage portion with its posture (or direction) set at randomly. When the passage defining member is subjected to vibration by activating the needle conveyor means, the needles in the needle storage portion proceed along the needle path and reach the selecting means in order. The needles in the certain posture meeting the predetermined condition are exclusively allowed to pass the select means while maintaining the posture. Accordingly, all the needles, after passing the select means, reach the needle discharge portion in the same posture meeting the above condition. Hence, the needles are supplied to the needle discharge portion one by one in the same posture.

With this arrangement, expensive means such as detector means for detecting the posture of the needle and drive means for allowing the needle in an improper posture to fall off from the needle path are not required. In other words, accurate supply of needles in the needle storage portion to the needle discharge portion one by one in the proper posture can be realized with a simplified and inexpensive arrangement by allowing the passage defining member to vibrate and providing the needle path of a certain shape. Thus, automation or labor reduction in the field of manufacturing sutures attached with needles and the like is attainable.

Preferably, the select means may include a left/right selecting unit for allowing the needle with an intermediate portion curved in a predetermined direction to pass while maintaining the posture. With this arrangement, needles in the improper posture in which the intermediate portion is curved in a direction opposite to the predetermined position are not allowed to pass the left/right selecting unit. Thus, when reaching the needle discharge portion via the left/right selecting unit, all the needles are set in a posture in which the intermediate portion is curved in the predetermined direction.

More preferably, the left/right selecting unit may have a narrow path of a width smaller than the size of the needle in a direction perpendicularly crossing a needle transport direction, the width of the narrow path may be set such that the center of gravity of the needle lies on the narrow path when the needle is transported with the intermediate portion thereof lying on the narrow path, and the center of gravity of the needle is offset from the narrow path when the needle is transported with the intermediate portion thereof deviated from the narrow path.

With this arrangement, the needles whose intermediate portion lying on the narrow path can pass the narrow path while maintaining the posture, whereas the needles whose intermediate portion is deviated from the narrow path fall off from the narrow path since the center of gravity of the needle is offset from the narrow path. In other words, the selection of needles can be executed effectively by considering where the center of gravity of the needle is located when the needle passes the narrow path.

More preferably, the narrow path may be arranged at a level higher than the needle storage portion and a slope adjoining the narrow path may be provided for guiding the needle falling off from the narrow path toward the needle storage portion. Thereby, the needles which have been ejected from the narrow path can be automatically collected in the needle storage portion. Accordingly, an additional operation of manually returning the needles which failed to pass the narrow path to the needle storage portion can be omitted, resulting in a further improvement on workability of the needle supply device.

Also, it may be preferable that the left/right selecting unit is a through hole formed in a side wall constituting the needle path, and that the through hole has a size such that a point or an end of the needle can enter and the intermediate portion of the needle cannot enter, whereby ejecting the needle outside the needle path via the through hole when the point or the end of the needle enters the through hole, and allowing the needle to pass by the through hole when the needle does not enter the through hole.

With this arrangement, the needle whose point or end opposes to the side wall are ejected from the needle path after entering the through hole via the point or the end. On the contrary, the needle whose intermediate portion opposes to the side wall are allowed to pass by the through hole while maintaining the posture, since the needle in the above posture does not enter the through hole. Accordingly, the selection of needles can be performed effectively by utilizing the curved shape of the needle.

Preferably, the left/right selecting unit may be a partition wall for dividing the needle path along the direction perpendicularly crossing the needle transport direction into two regions, one region being an upstream passage communicating with the needle storage portion and the other region being a downstream passage communicating with the needle discharge portion. The partition wall may be formed with a through hole having a size such that the point or the end of the needle can enter and the intermediate portion of the needle cannot enter, whereby allowing the needle to reach the downstream passage in a state that the direction of the needle is reversed by about 180 degree while passing the through hole when the point or the end of the needle enters the through hole, and allowing the needle to reach the downstream passage without changing the posture when the needle does not enter the through hole.

With this arrangement, the needles in the proper posture, in which the intermediate curved portion opposes to the partition wall, are transported to the downstream passage, while maintaining the posture. Contrary to this, the needles in the improper posture, in which the intermediate curved portion opposes to the direction opposite to the partition wall, can also be transported along the downstream passage and then reach the needle discharge portion after having the posture corrected to the proper state, because the direction of the needle is reversed by about 180 degree while passing the through hole of the partition wall via the point or the end of the needle.

This arrangement is advantageous in efficiently supplying needles, because the improper posture of the needle can be corrected by utilizing the curved shape of the needle.

More preferably, a side wall of the downstream passage may be formed with a through hole of a size such that the point or the end of the needle can enter and the intermediate portion of the needle cannot enter, whereby ejecting the needle outside the needle path via the through hole when the point or the end of the needle passing along the downstream passage enters the through hole, and allowing the needle to pass along the downstream passage when the needle does not enter the through hole.

With this arrangement, even though there should be the case where needles reach the downstream passage without reversing the direction in passing through the hole of the partition wall (i.e., without correcting the improper posture), such needles are ejected outside the needle path via the through hole formed in the side wall of the downstream passage. Thus, reliability of the needle selection can be further improved.

More preferably, the select means may include a front/rear selecting unit for allowing the needle to pass in a predetermined state that the point or the end of the needle is directed forward with respect to the needle transport direction. Thereby, all the needles after passing the front/rear selecting unit can be supplied to the needle discharge portion in a state that the point thereof is directed forward.

More preferably, the needle path formed with the front/rear selecting unit may include a bottom wall and a side wall upwardly extending from the bottom wall for supporting the needle in a tilted state, the side wall may be formed with a hollow portion extending from an upper surface of the bottom wall or from a proximity thereof to a predetermined height level, and the height level and the configuration of the hollow portion are set so as to allow the needle to pass over the hollow portion with the point thereof being in contact with an upper portion of the side wall above the hollow portion when the needle moves along the bottom wall in a state that the intermediate portion is in contact with the upper surface of the bottom wall and the point thereof is directed forward, and to allow the needle in a posture other than the above posture (i.e., the needle whose end is directed forward) to be trapped in the hollow portion and ejected outside the needle path.

With this arrangement, the front/rear selection can be executed with an inexpensive construction, and the needles whose intermediate portion is in contact with the bottom wall and whose point is directed forward with respect to the needle transport direction can be exclusively supplied to the needle discharge portion.

More preferably, as specific means for ejecting the needles in the improper posture, the hollow portion may be a through hole communicating with the side wall, so that the needle with the point thereof coming into the through hole may fall off from the bottom wall via the through hole. Alternatively, the widthwise size of the bottom wall may be set so as to deviate the center of gravity of the needle from the bottom wall to the side away from the sidewall by allowing the needle to enter the hollow portion. In the latter case, the hollow portion may be a through hole or a recess. In either case, the needle is caused to fall off to the side away from the side wall by shifting the center of gravity of the needle when it is trapped in the hollow portion.

In the above needle supply device, the shape of the needle path is not limited to any specific one. Preferably, the needle path may have a substantially spiral shape, and the needle storage portion may be arranged at one of a center portion and a circumferentially outer portion of the needle path, and the needle discharge portion may be arranged at the other one. With this arrangement, compared to the case where the needle path is formed into a linear shape, the needle supply device can be set in a reduced space, while securing a sufficiently long passage.

Preferably, the needle supply device may further comprise needle detector means for detecting the needle discharged on the needle discharge portion and conveyor control means for controlling the needle conveyor means to temporarily suspend a transport operation when the needle detector means detects the presence of the needle.

With this arrangement, there can be eliminated the drawback that a next needle is being discharged onto the needle discharge portion before the previously discharged needle is transferred from the needle discharge portion. Hence, the needle supply can be assuredly executed one by one.

BEST MODE FOR CARRYING OUT THE INVENTION

A first embodiment according to this invention is described with reference to FIGS. 1 to 12 and 18.

Figure 18:
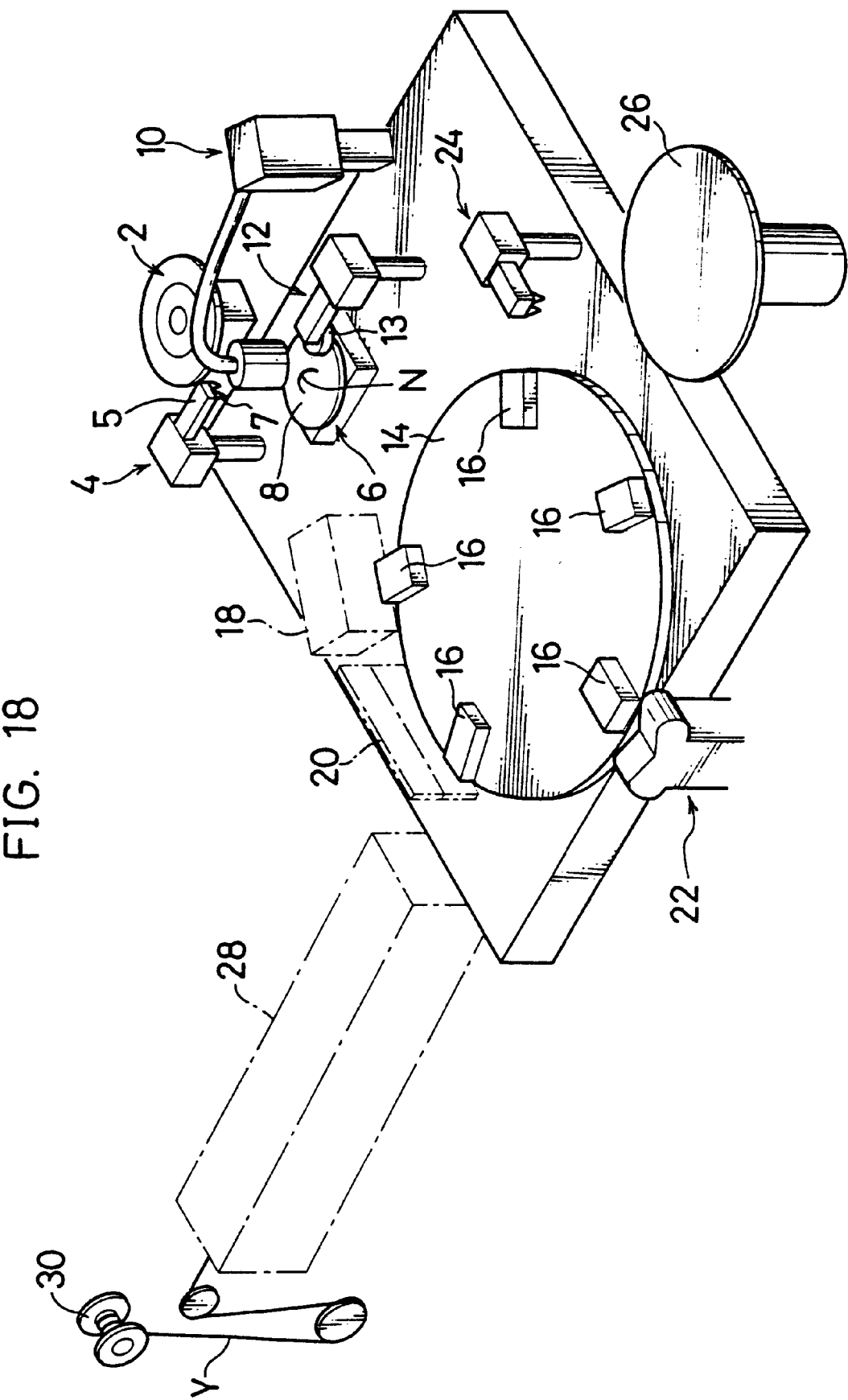
FIG. 18 is a perspective view of an entire arrangement of a needle-attached suture manufacturing apparatus provided with the needle supply device according to this invention.

FIG. 18 is a diagram showing an entire arrangement of a needle-attached suture manufacturing apparatus provided with a needle supply device 2 according to this invention. The needle-attached suture manufacturing apparatus comprises, besides the needle supply device 2, a needle transport device (needle transport means) 4, a needle direction adjuster 6, a needle pick-up device 12, a turntable 14, a needle end adjuster 18, a needle swaging die 20, an inspector 22, a needle discharge device 24, a needle discharge table 26, and a suture supply device 28.

The needle transport device 4 has a pivotal arm 5. At the point of the pivotal arm 5, there is mounted a needle chuck 7. The needle chuck 7 is adapted for picking up a needle N which is supplied to a predetermined position (details of which are described later) on the needle supply device 2 and is adapted for transporting the needle N onto the needle direction adjuster 6 by a pivotal rotation about a vertical pin of the pivotal arm 5 and a vertical movement thereof.

Note that the needle N handled by the needle-attached suture manufacturing apparatus has a shape substantially curved into an arc and the end thereof has a thickness larger than the point. The end of the needle N is formed with a hole axially opened, through which a suture is to be inserted.

The needle direction adjuster 6 has an adjuster table 8 and an image recognizer 10. The adjuster table 8 is set such that it is movable forward/backward and rightward/leftward on a horizontal plane and can make turns while carrying the needle N. The image recognizer 10 comprises a CCD or its equivalent, and is adapted for recognizing an image of a needle placed on the adjuster table 8. Moving the adjuster table 8 to render the recognized image coincident with a predetermined target image minutely adjusts the direction (posture) and position of the needle N on the adjuster table 8.

The needle pick-up device 12 is constructed such that a needle drawing portion 13 is mounted at the point of a pivotal arm. The needle drawing portion 13 attracts the needle N whose direction is precisely adjusted on the adjuster table 8, using an air suction force. While securely attracting the needle N to the needle drawing portion 13, the pivotal arm of the needle pick-up device 12 is rotated to supply the needle N to a needle retainer 16 mounted on the turntable 14.

The turntable 14 is driven to make turns on a base block, and is provided with a plural needle retainers 16 along a circumference thereof. Each needle retainer 16 is provided to hold the needle N supplied from the needle pick-up device 12. Accompanied by a turn of the turntable 14, the corresponding needle retainer 16 transports the needle N to the needle end adjuster 18, the needle swaging die 20, the inspector 22, and the needle discharge device 24 in this order.

The needle end adjuster 18 is adapted for pushing the end of the needle N held on the needle retainer 16 placed on a predetermined position against a retaining force of the needle retainer 16, thereby precisely positioning the end of the needle N.

The needle swaging die 20 is adapted for swaging the end of the needle N from upward and downward in a state that a suture Y supplied from the suture supply device 28 is inserted in the insertion hole formed at the end of the needle N which is securely positioned on the needle retainer 16. Thereby, the suture Y and the needle N are attached with a predetermined pressing (swaging) force to produce a needle-attached suture. The suture supply device 28 is constructed such that the suture Y wound around a bobbin 30 is drawn out by a certain length and cut thereafter to insert the suture Y of the certain length into the insertion hole of the needle N which is securely held on the needle retainer 16.

The inspector 22 is adapted for inspecting whether the attaching strength of the suture Y to the needle N is sufficient by exerting the suture Y a tensile load directing downward.

The needle discharge device 24 is provided with a needle chuck at the point of a pivotal arm. The needle chuck picks up the needle N (attached with the suture Y) on the needle retainer 16 and discharges the needle N onto the needle discharge table 26.

Next, a specific arrangement of the needle supply device 2 is described with reference to FIGS. 1 to 12.

The needle supply device 2 has a passage defining member 32 and a rotary vibrator (needle conveyor means) 34. The rotary vibrator 34 has a support pin 36 jutting upward. A center portion of the passage defining member 32 is connected to the support pin 36. When the rotary vibrator 34 is activated, the passage defining member 32 is subjected to vibration along the circumference thereof.

The passage defining member 32 has a horizontally flat base 38, a passage defining wall 40 provided upright on the base 38, and a rim wall 41 which is provided upright circumferentially along the radially outermost rim (shown in FIG. 2) thereof. The passage defining wall 40 has, in a top plan view, a substantially spiral form. The passage defining wall 40 comprises, from the radially inner side toward the outer side, a needle storage portion 42, an upstream passage 44, and a downstream passage 46 in this order. The needle storage portion 42, the upstream passage 44, and the downstream passage 46 are communicated with one another in this order, and the elevating level thereof is increased in this order. At the end of the downstream passage 46, there is provided a needle discharge tray (needle discharge portion) 55. When the passage defining member 32 is subjected to a rotational vibration by driving the rotary vibrator 34, needles N stored in the needle storage portion 42 climb over the upstream passage 44 and then the downstream passage 46, thereby being supplied to the needle discharge tray 55.

A conventional conveyor which is used in transporting relatively small parts such as nuts may be applicable as the rotary vibrator 34.

On the way of the upstream passage 44 and the downstream passage 46, there are provided a first selecting unit (left/right selecting unit) 48, a second selecting unit (left/right selecting unit) 50, and a third selecting unit (front/rear or point/end selecting unit) 52 each having a certain shape for selecting the needles N.

The structure of the first selecting unit 48 is described in detail with reference to FIGS. 3 and 4. The first selecting unit 48 is provided on the way of the downstream passage 44, and comprises a narrow path 44a and a slope 54 arranged side by side (in a direction orthogonal to the needle transport direction).

The narrow path 44a has a width smaller than the other portion of the upstream passage 44 and is connected solely to a radially outward portion of the upstream passage 44. The slope 54 is tilted downward from the narrow path 44a and is connected to the needle storage portion 42 provided centrally in the needle supply device 2.

Figure 3A:
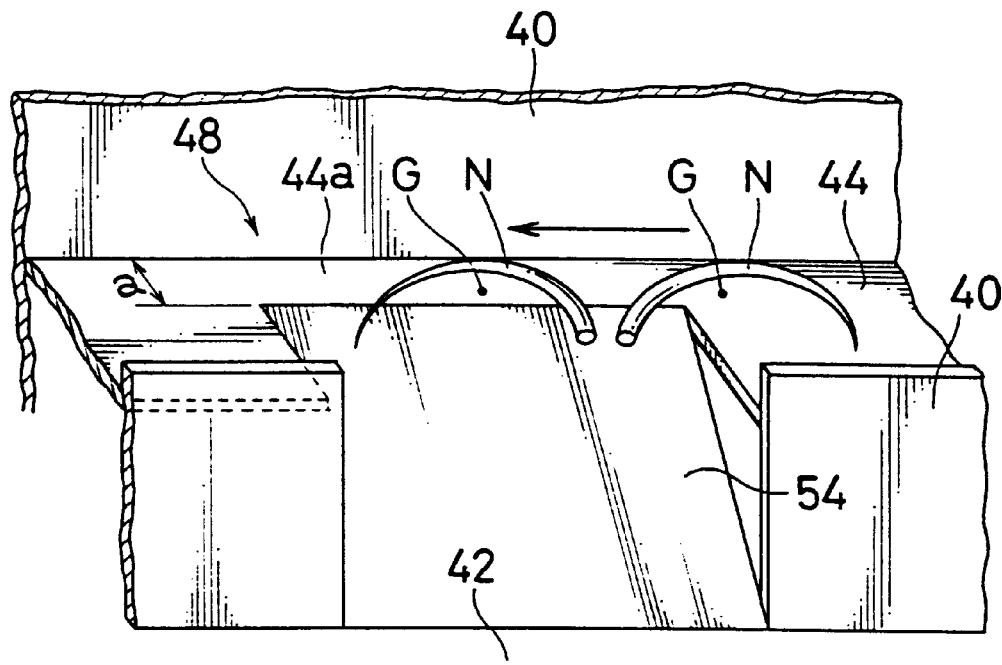
FIG. 3A is a perspective view showing a state in which a needle passes a narrow path formed in a first selecting unit provided in the needle supply device with the center of gravity of the needle lying on the narrow path.
Figure 3B:
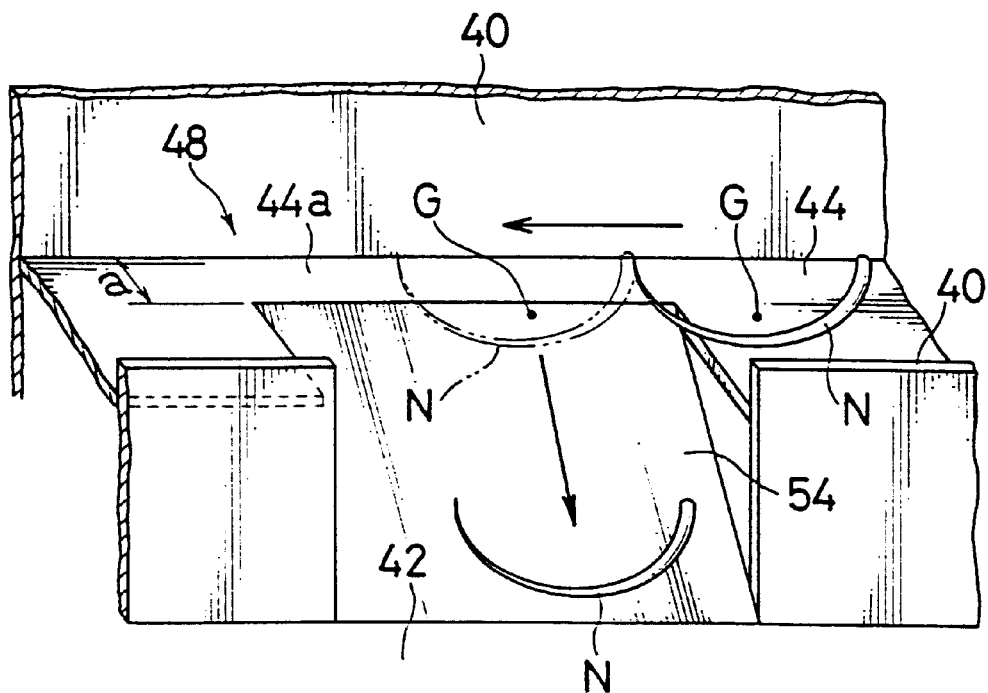
FIG. 3B is a perspective view showing a state in which a needle falls off from the narrow path with the center of gravity of the needle deviated from the narrow path.
Figure 4A:
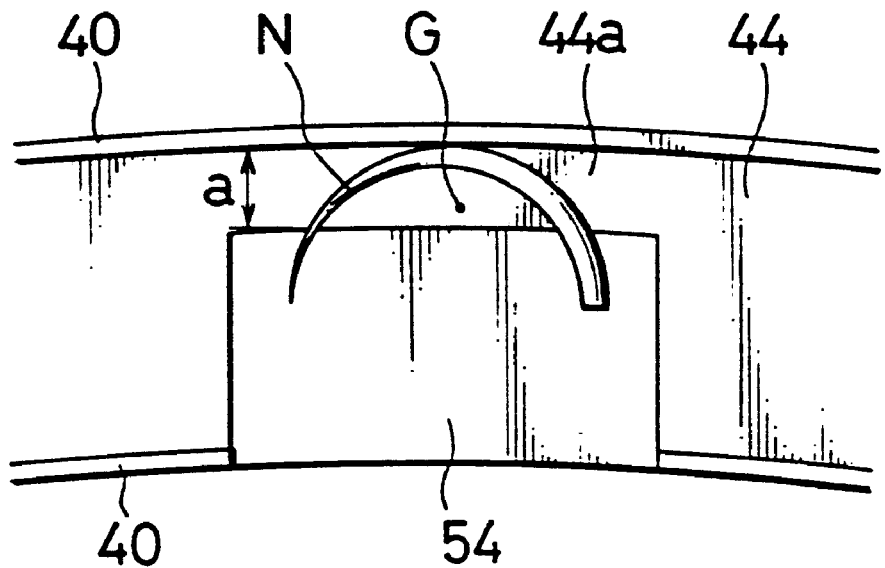
FIG. 4A is a plan view illustrating a state in which the center of gravity of the needle lies on the narrow path.

The widthwise dimension a of the narrow path 44a is set to meet the following requirements:

① In the case where the needle N moves along the narrow path 44a in contact with the passage defining wall 40 which is provided radially outward (in FIG. 3, shown as the rear side), as shown in FIGS. 3A and 4A, the center of gravity G of the needle N lies on the narrow path 44a when an intermediate portion of the needle N (i.e., curved portion of the needle) keeps in contact with (or opposes to) the passage defining wall 40.

Figure 4B:
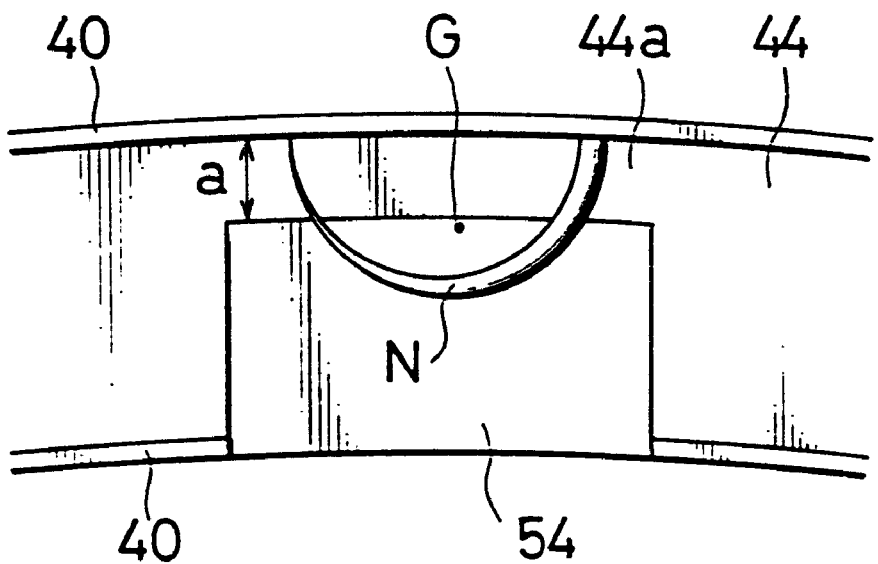
FIG. 4B is a plan view illustrating a state in which the center of gravity of the needle is deviated from the narrow path.

② In the above case and when at least either one of the point and the end of the needle N is in contact with the passage defining wall 40, or more than one needle is carried in an overlapped state, as shown in FIGS. 3B and 4B, the center of gravity G of the needle N is offset radially inward from the narrow path 44a (i.e., located on the slope 54).

Figure 5:
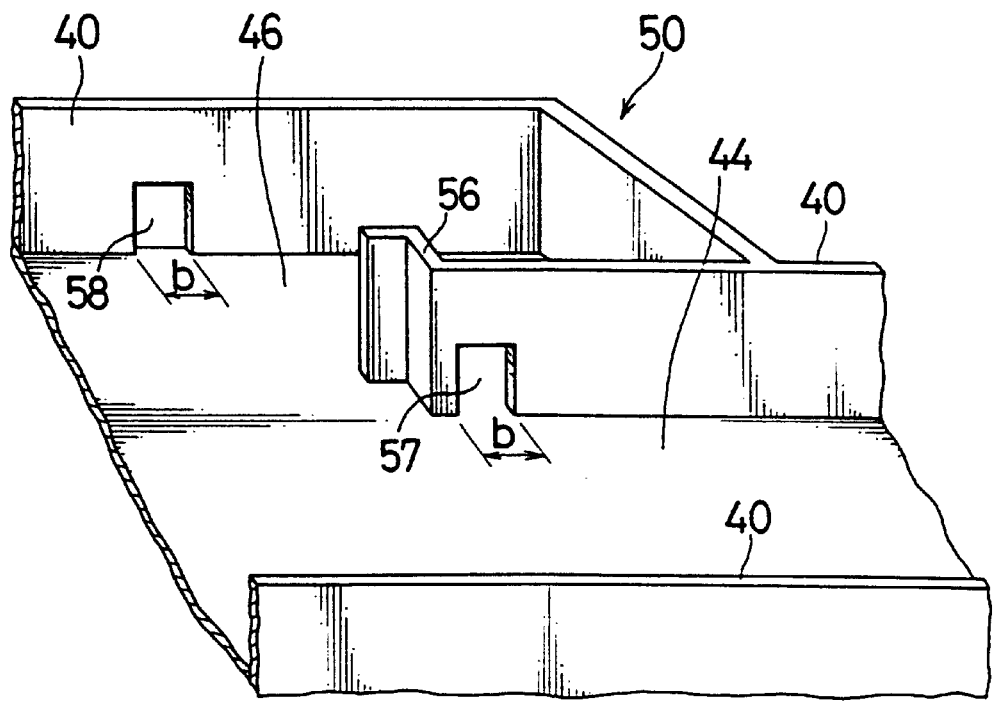
FIG. 5 is a perspective view of a second selecting unit provided in the needle supply device.

The structure of the second selecting unit 50 is described in detail with reference to FIGS. 5 to 7. The second selecting unit 50 is provided in a boundary portion between the upstream passage 44 which is located radially inward and the downstream passage 46 which is located radially outward, and is provided with a partition wall 56 separating the passages 44 and 46. The passages 44 and 46 are communicated with each other radially at a further point of the partition wall 56.

The partition wall 56 and the passage defining wall 40 which is located radially outward of the downstream passage 46 are respectively formed with through holes 57 and 58. The widthwise dimension b of the through hole 57 (58) is set such that the intermediate portion (curved portion) of the needle N cannot enter the hole 57 (58) (see FIG. 6) and that the point or end of the needle N can enter the hole 57 (58) (see FIGS. 7A and 7B).

Figure 8:
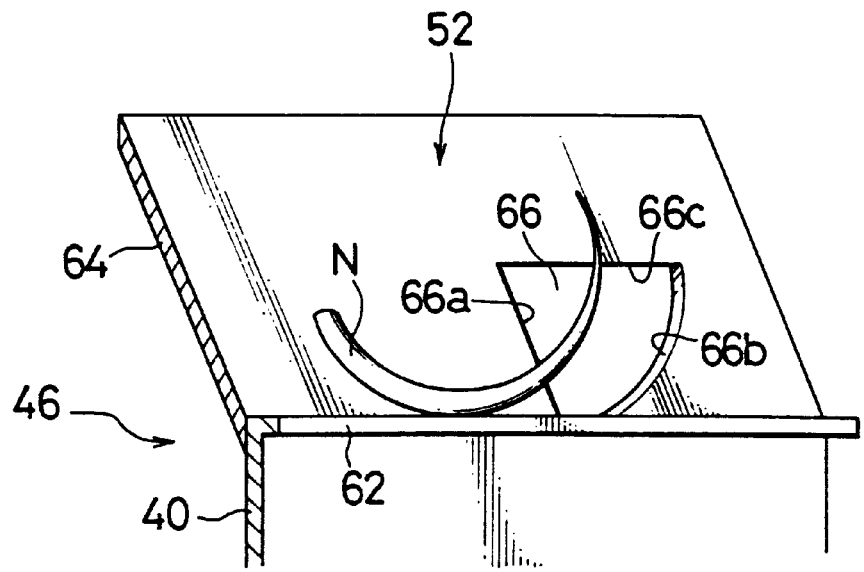
FIG. 8 is a perspective view of a third selecting unit provided in the needle supply device.
Figure 10:
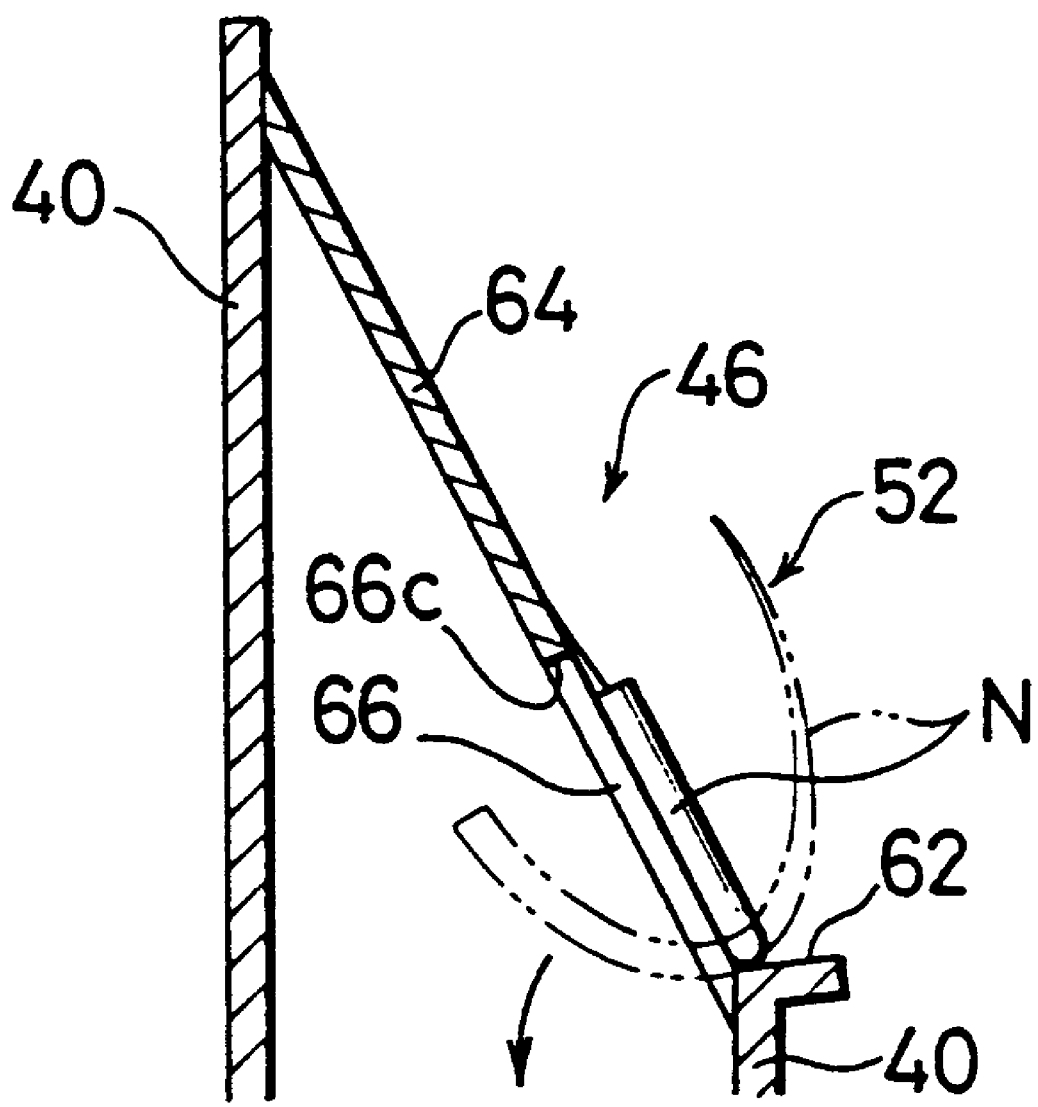
FIG. 10 is a cross sectional view of the third selecting unit taken along the line B—B in FIG. 9.

A bottom wall of the downstream passage 46 is tilted upward as approaching downstream to finally form a side wall 64 shown in FIGS. 8 and 10. The passage defining wall 40 is constructed such that an upper end of the outermost passage defining wall 40 constitutes a bottom wall 62. The bottom wall 62 and the side wall 64 define the downstream passage 46. The needle N moves along the bottom wall 62 while leaning on the side wall 64. The third selecting unit 52 is provided on the way of the downstream passage 46.

Figure 1:
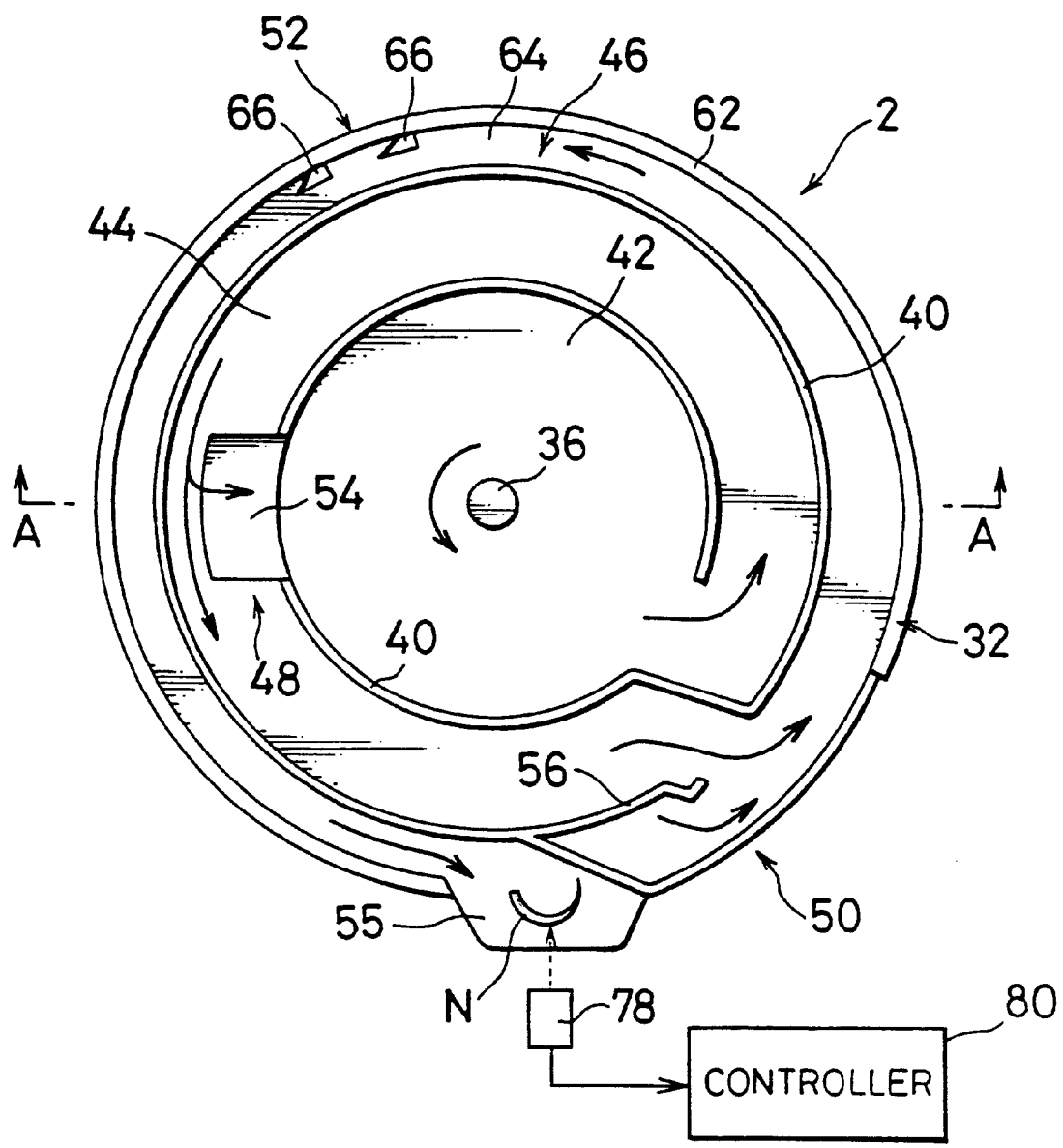
FIG. 1 is a plan view of a needle supply device as a first embodiment according to this invention.
Figure 2:
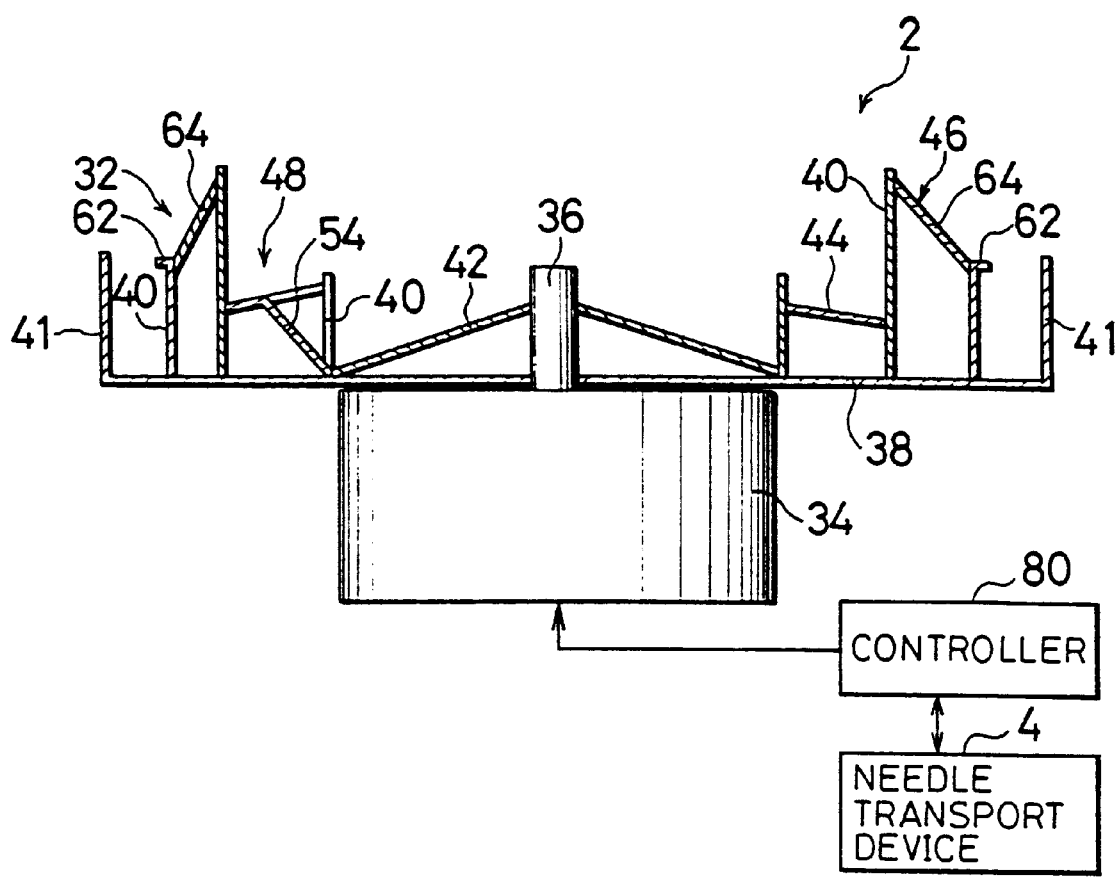
FIG. 2 is a cross sectional view of the needle supply device taken along the line A—A in FIG. 1.

In the third selecting unit 52, the side wall 64 is formed with a desired number of through holes 66 (in FIG. 1, two holes are shown). The through hole 66 is enclosed, as shown in the embodiment of FIG. 8, by an upright edge 66a extending linearly straight upward from the bottom wall 62, a circular edge 66b extending also from the bottom wall 62 in a substantially arc shape at the downstream side of the upright edge 66a, and a horizontal edge 66c horizontally connecting an upper end of the upright edge 66a and that of the circular edge 66b. The radius of the curvature of the circular edge 66b is substantially equal to that of the needle.

Figure 9:
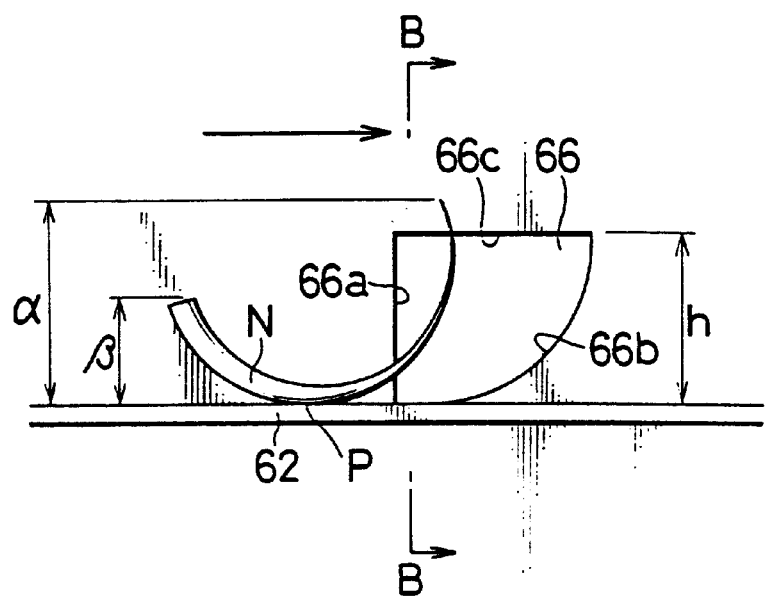
FIG. 9 is a front view of the third selecting unit.

As shown in FIG. 9, the height level h of the horizontal edge 66c from the bottom wall 62 is smaller than the height level α of the needle N from a point P to the point thereof, and is greater than the height level β of the needle N from the point P to the end thereof. Note that the needle N moves in a state that the intermediate portion is in contact with an upper surface of the bottom wall 62 at the contact point P.

The difference between the values α and β is due to the fact that the end of the needle N has a thickness larger than the point thereof, and hence the center of gravity of the needle is shifted to the end.

In the vicinity of the needle discharge tray 55, there is provided a needle detector 78. The needle detector 78 detects whether the needle N is discharged on the needle discharge tray 55, and outputs a detection signal to a controller 80 when the needle N is discharged on the tray 55. The controller (conveyor controlling means) 80 comprises a microcomputer, and is constructed such that operations of the needle transport device 4 and the rotary vibrator 34 are controlled based on a detection signal from the needle detector 78.

Next, operations of the needle supply device having the above arrangement are described.

First, a multitude of needles N are thrown into the needle storage portion 42 in a state that the posture or the direction thereof is set irregularly. When the rotary vibrator 34 is driven, the rotary vibrator 34 allows the entirety of the passage defining member 32 to shake in the circumferential direction. Thereby, the needles N in the needle storage portion 42 proceed along the upstream passage 44 and the downstream passage 46 in this order to reach the needle discharge tray 55.

At this time, each needle N proceeds along the upstream passage 44 while keeping in contact with an inner circumference of the passage defining wall 40 separating the upstream passage 44 and the downstream passage 46 due to the centrifugal force resulting from a rotational vibration of the rotary vibrator 34. When the needles N proceed along the upstream passage 44, the direction of the needles N is individually irregular. Accordingly, as shown in FIGS. 3A and 4A, there exist, in the upstream passage 44, needles N with the intermediate curved portion thereof in contact with the passage defining wall 40 (hereinafter referred to as a first state needle), needles N in a state in which at least either the point or end of the needle is in contact with the passage defining wall 40 (hereinafter referred to as a second state needle), and needles N which overlap each other or one another.

When the above needles in the various states reach the first selecting unit 48, the first state needles N can pass the narrow path 44a without falling therefrom, since the center of gravity G of the needle lies on the narrow path 44a. Contrary to this, the second state needles N and the needles in an overlapped state fall off from the narrow path 44a, since the center of gravity G of these needles is deviated on the slope 54. As a result, the needles which cannot pass the first selecting unit 48 fall off over the slope 54 and return to the needle storage portion 42. Accordingly, when moving along the first selecting unit 48 of the upstream passage 44, the needles N in the first state are allowed to pass, while the needles N in the second state are ejected.

Even if the centrifugal force cannot be utilized, e.g., the needle passage is straight, the needles N can move along the needle passage in contact with the passage defining wall 40 by inclining a bottom wall constituting the passage downward in such a direction as to lower a portion closer to the passage defining wall 40.

The needles N which pass the first selecting unit 48 then approach the second selecting unit 50. At this time, since a selection is already done in the first selecting unit 48, the needles N approaching the second selecting unit 50 are all supposed to be in the first state, i.e., in a state in which the intermediate curved portion is in contact with the passage defining wall 40, as shown in FIG. 6. However, there should be considered the case where the first selecting unit 48 fails to complete the selection. Specifically, in such a case, there still exist the needles in the second state in which at least one of the point and the end of the needle is in contact with the passage defining wall 40, as shown in FIG. 7A. The second selecting unit 50 is provided to execute a further selection, thereby improving the accuracy of selection.

Figure 6:
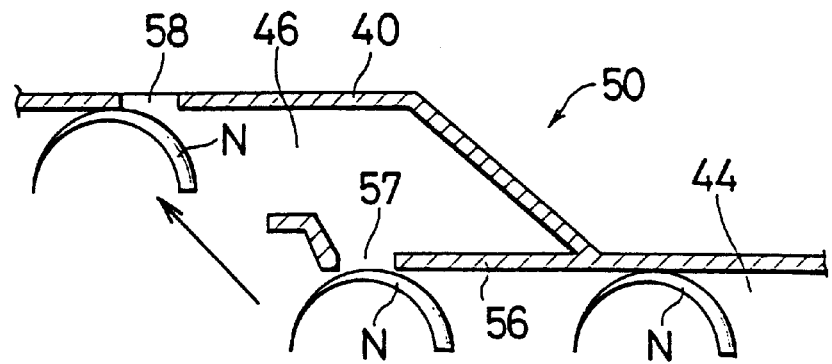
FIG. 6 is a cross sectional plan view showing a state in which a needle passes the second selecting unit in a proper posture.
Figure 7A:
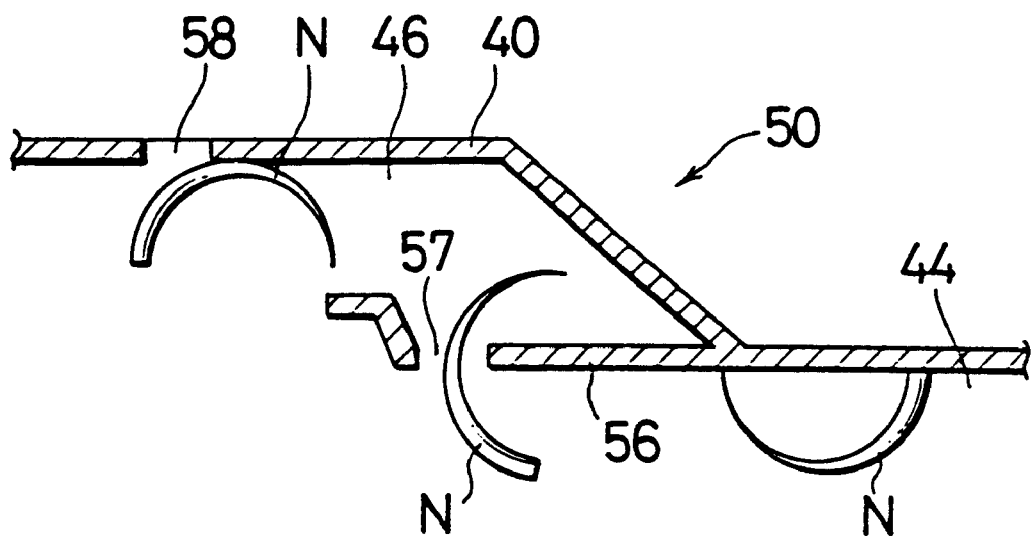
FIG. 7A is a cross sectional plan view showing a state in which a needle reverses its direction while passing a through hole of a partition wall in the second selecting unit.

More specifically, as shown in FIG. 6, the needle N in the first state cannot enter the through hole 57 formed in the partition wall 56 of the second selecting unit 50. Accordingly, the needle N moves ahead to the downstream passage 46. Contrary to this, as shown in FIG. 7A, the needle N in the second state can enter the through hole 57 via the point or the end thereof. While entering the through hole 57, the needle N has its posture rotated by about 180 degree. Thereby, the needle N moves ahead to the downstream passage 46 after the direction thereof is automatically corrected (i.e., set in the first state).

Figure 7B:
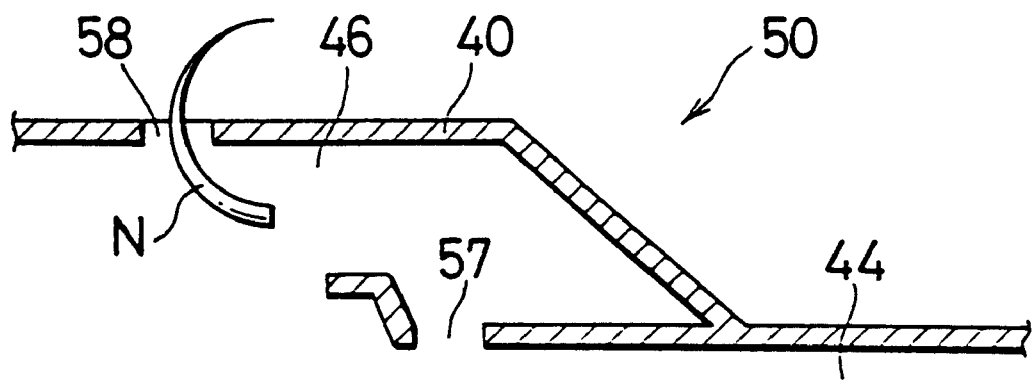
FIG. 7B is a cross sectional plan view showing a state in which a needle is ejected while passing a through hole in a wall constituting a downstream passage in the second selecting unit.

Further, as shown in FIG. 7B, the needle N whose direction is not properly corrected due to an insufficient rotation enters the through hole 58 via the point or the end thereof and is ejected from the passage. Accordingly, at a final stage after the second selecting unit 50, the needles N in the first state, i.e., which are set in the proper posture are exclusively supplied to the downstream passage 46.

As approaching the downstream passage 46, the member constituting the bottom wall is raised upward to constitute the side wall 64 in the second selecting unit 50. Accordingly, as coming closer to the second selecting unit 50, the needle N gradually stands up. Finally, the needle N moves toward the third selecting unit 52, while leaning on the side wall 64 and moving along the bottom wall 62 formed on the upper end of the outermost passage defining wall 40.

Figure 11A:
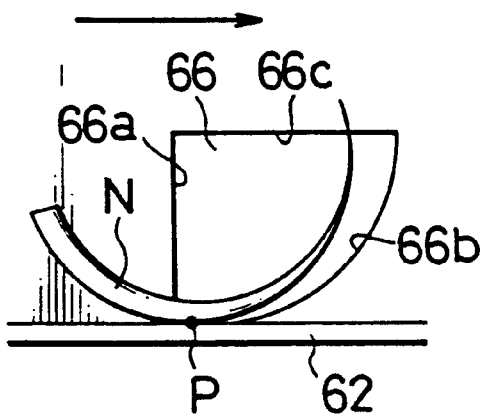
FIGS. 11A and 11B are front views showing a state in which a needle with the point thereof directed forward passes the third selecting unit.
Figure 11B:
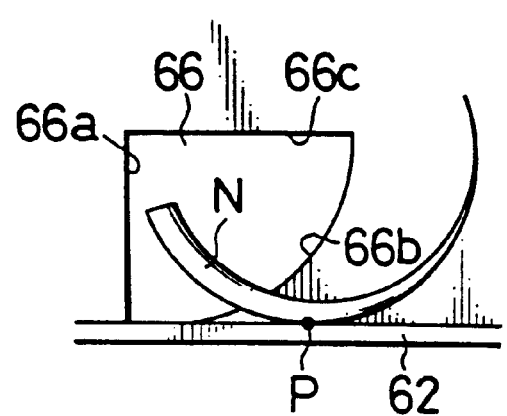
Figure 12A:
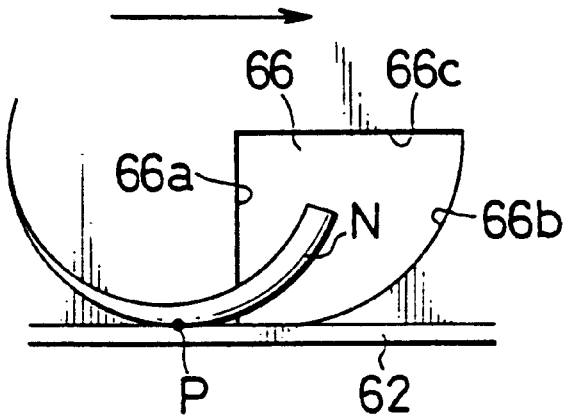
FIGS. 12A and 12B are front views showing a state in which a needle with the end thereof directed forward reaches the third selecting unit.
Figure 12B:
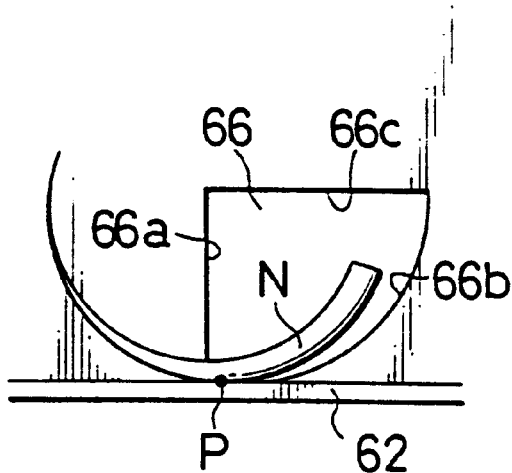

Among the needles N approaching the third selecting unit 52, there exist the needles N with the point thereof moving ahead as shown in FIGS. 8, 9, and 11, and the needles N with the end thereof moving ahead as shown in FIG. 12. The former needle N moves along the third selecting unit 52 in a state where the point is in contact with an upper portion above the horizontal edge 66c of the through hole 66 in the side wall 64 (see solid lines in FIG. 10 and FIGS. 11A and 11B). Accordingly, the needle N can assuredly pass along the bottom wall 62 without entering the through hole 66.

Contrary to the former needle N, the latter needle N enters the through hole 66 via the end thereof at a point of time when the point P of the needle N in contact with the bottom wall 62 reaches an area enclosed by the upright edge 66a and the circular edge 66b. This is because the end of the needle which first approaches the third selecting unit 52 has a height lower than the horizontal edge 66c. Thus, the latter needle N loses the balance and falls off from the bottom wall 62 into the through hole 66 (see phantom lines in FIG. 10 and FIGS. 12A and 12B). In this way, the third selecting unit 52 allows the needles N with the point thereof moving forward to pass, while ejecting the needles N with the end thereof moving forward.

Thus, merely the needles N which pass the first, second, and third selecting units 48, 50, and 52 can reach the needle discharge tray 55. That is, the needles N with the intermediate curved portion thereof directing radially outward of the passage defining member 32 and the point thereof directing forward are exclusively discharged onto the needle discharge tray 55. Each time the needle N meeting the above conditions is discharged onto the needle discharge tray 55, the needle detector 78 outputs a detection signal to the controller 80.

The controller 80 controls the rotary vibrator 34 to temporarily suspend its driving upon receiving the detection signal, and outputs a command signal to the needle transport device 4 to move the needle chuck 7 provided at the point of the pivotal arm 5 to the needle discharge tray 55, thereby allowing the needle chuck 7 to pick up the needle N discharged on the needle discharge tray 55.

Upon confirming that the needle N is transported by the needle transport device 4, the controller 80 controls the rotary vibrator 34 to initiate a driving again. The controller 80 executes the above-mentioned operations to eliminate the possibility that a plural needles N are discharged on the needle discharge tray 55 at the same time, to supply the needles N in the proper posture one by one to the needle discharge tray 55, and to transfer the needle N to the needle chuck 7 assuredly.

The needle N, which is picked up by the needle chuck 7 with the proper posture retained, is transferred to a predetermined position by a pivotal rotation of the pivotal arm 5, and thereafter, is subjected to a suture attaching operation by the manufacturing apparatus shown in FIG. 18.

In the needle supply device according to this invention, merely placing needles N in the needle storage portion 42 arranged in the center of the needle supply device allows automatic supply of the needles N to the needle attached suture manufacturing apparatus. Further, an expensive sensor for detecting the posture of the needle N is not required. A simplified construction in which the passage defining member 32 constituting a passage of a certain shape is subjected to a rotational vibration can perform an accurate selection of needles N.

Next, a second embodiment according to this invention is described with reference to FIGS. 13 to 17.

In this embodiment, the side wall 64 of the third selecting unit 52 is formed at a lower end thereof with a recess 68 in place of the through hole 66, and a through hole 70 is formed continuously from the recess 68.

Figure 13:
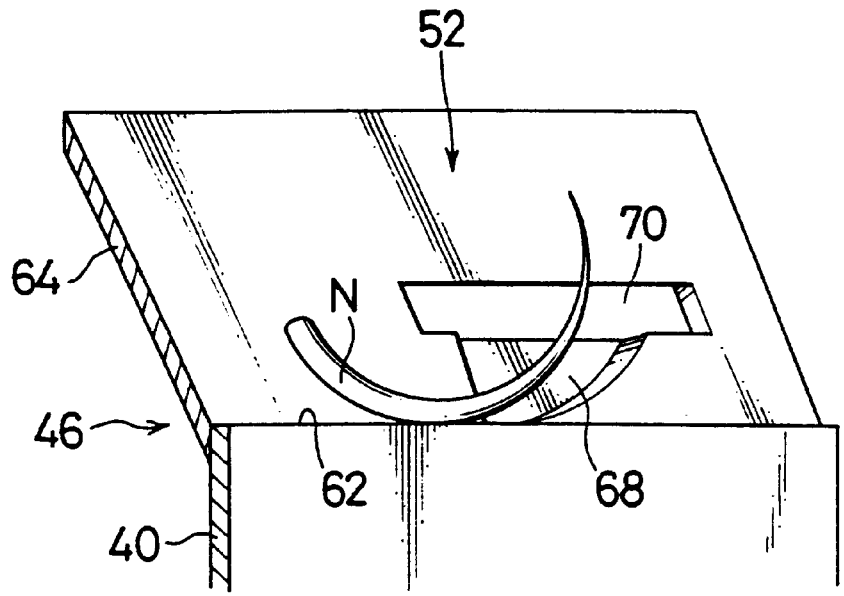
FIG. 13 is a perspective view of a third selecting unit in a needle supply device as a second embodiment.
Figure 14:
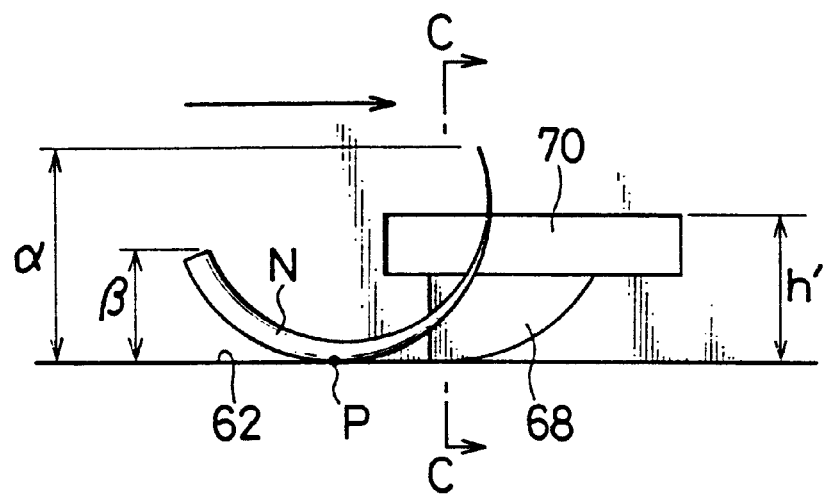
FIG. 14 is a front view of the third selecting unit in the second embodiment.
Figure 15:
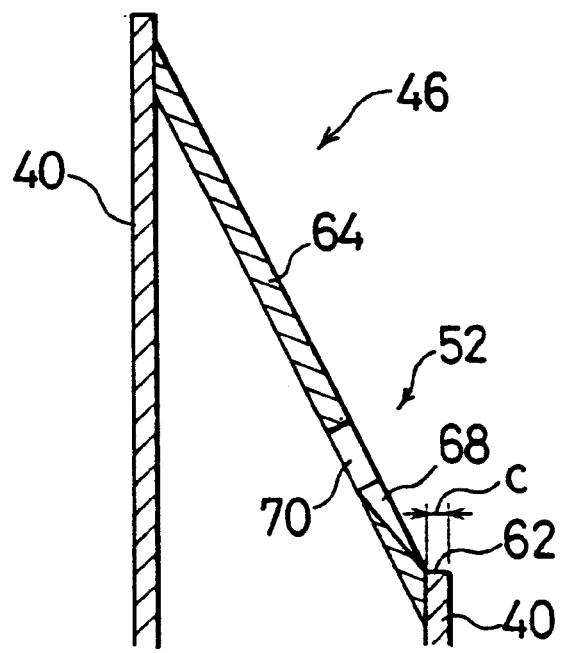
FIG. 15 is a cross sectional view of the third selecting unit taken along the line C—C in FIG. 14.

As shown in FIGS. 13 and 14, the recess 68 has a shape in front view substantially identical to the shape of the through hole 66 in side view, and has such a shape in cross section so as to deepen the recess as approaching an upper end, as shown in FIG. 15. The through hole 70 extends from the upper end of the recess 68. The height level h' of the through hole 70 from the bottom wall 62 to the upper end is smaller than the height level α of the needle N from the contact point P to the point thereof, and is greater than the height level β to the end thereof. The needle N moves along the bottom wall 62 in contact therewith at the point P.

The widthwise dimension d of the bottom wall 62 is set so as to be substantially coincident with the diameter of the needle N. Thereby, there can be prevented a plural needles N from moving in an overlapped state.

Figure 16:
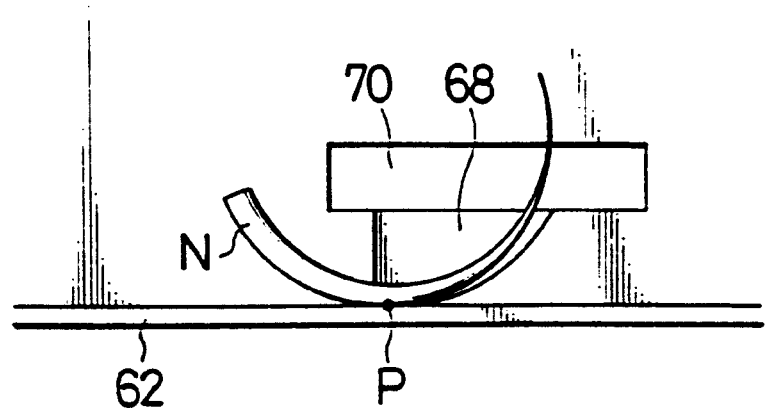
FIG. 16 is a front view showing a state in which a needle with the point thereof directed forward passes the third selecting unit in the second embodiment.
Figure 17A:
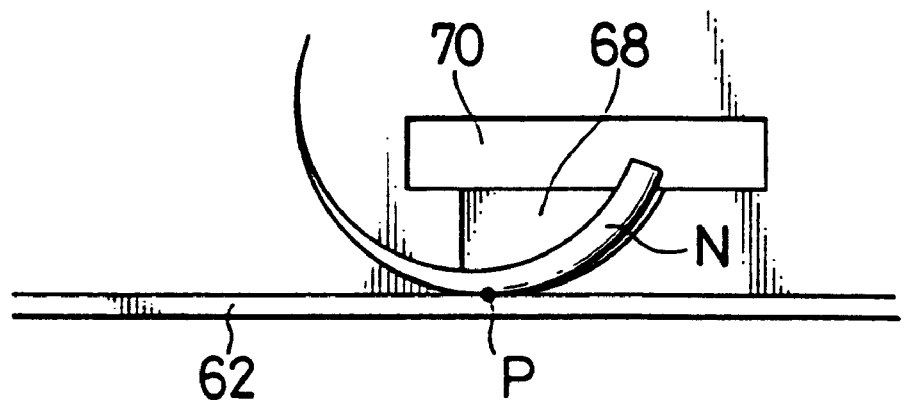
FIG. 17A is a front view showing a state in which a needle with the end thereof directed forward is trapped in a recess of the third selecting unit.
Figure 17B:
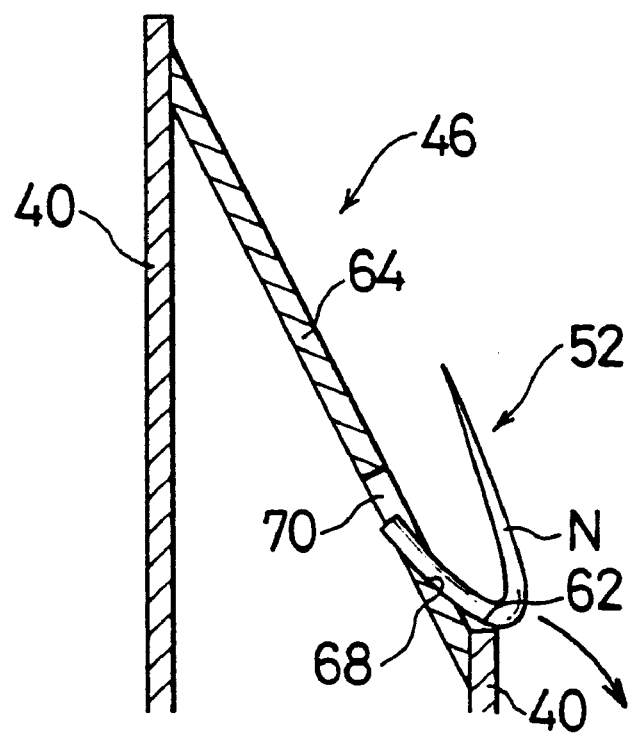
FIG. 17B is a cross sectional view of the needle shown in FIG. 17A.

Among the needles N reaching the third selecting unit 52, as shown in FIGS. 13, 14, and 16, the needle N whose point is directed forward moves in a state that the point is in contact with a region of the side wall 64 above the upper end of the through hole 70. Accordingly, the needle in the above state can pass the third selecting unit 52 without falling into the through hole 70 and tripping over the recess 68. Contrary to this, as shown in FIG. 17A, the needle N whose end is directed forward has the end trapped in the recess 68 at a point of time when the contact point P with the bottom wall 62 reaches the region forming the recess 68. This is because the end of the needle has a height lower than the through hole 70. Thereby, the needle N as a whole rotates by the amount corresponding to the trapped portion (see FIG. 17B) with respect to an instantaneous center P (FIG. 17A). Due to this rotation (angular displacement), the gravity center G of the needle N is deviated from the region above the bottom wall 62 to radially outward (in FIG. 17B to the right side), thereby causing the needle N to lose balance and then fall off from the bottom wall 62 and to be gathered in the inner side of the rim wall 41 (see FIG. 2).

The third selecting unit 52 in the second embodiment can also allow the needles N with the point thereof directing forward to pass, while ejecting the needles N with the end thereof directing forward.

The present invention is not limited to the above embodiments, but may take the following modifications and alterations.

(1) The needle passage may be straight. By linearly vibrating the needle passage, needles can be conveyed forward. However, as shown in FIG. 1, the spiral shaped needle passage is advantageous in view of reducing a space for the needle supply device and in securing a sufficient length for the passage.

Even if the case where the needle passage has a spiral shape, the location of the needle storage portion 42 and the needle discharge tray 55 is not limited to the center and the circumferentially outward position, respectively. Contrary to the embodiment, there can be considered an alteration in which the needle storage portion 42 is arranged at circumferentially outward and the needle discharge tray 55 is arranged centrally (i.e., the arrangement in which needles N are transported from radially outward to inward)

(2) One of the selecting units 48, 50, and 52 shown in the above embodiments may be omitted, considering the state of use of apparatus and required accuracy for selection. For instance, the first selecting unit 48 or the second selecting unit 50 may be omitted. In the case where the front/rear selection is not required, the third selecting unit 52 may be omitted. If the left/right selection is not required, the first and/or second selecting unit 48, 50 may be omitted.

The through hole 66 and the recess 68 may be formed into such a shape as to allow the needle N which moves in a state that both point and end thereof are in contact with the bottom wall 62 to enter the through hole 66 and the recess 68. In such case, it may be possible for the third selecting unit 52 to execute the left/right selection and the front/rear selection simultaneously, without providing the selecting units 48 and 50.

(3) In the case where it is assured that the posture of the needle is corrected in passing the through hole 57, the through hole 58 of the second selecting unit 50 may be omitted. Contrary to this, the partition wall 56 may be omitted, and the passage defining wall 40 may be formed merely with the through hole 58. In the latter case, the left/right selection is also executable. However, the selection by the provision of the partition wall 56 formed with the hole 57 aims at correcting the improper posture of the needle and allowing the needle after correcting the improper posture to move along the downstream passage 46, not for the purpose of ejecting the needles in the improper posture. Accordingly, compared to the case where the needles in the improper posture are ejected, selection of needles considering the posture correction is more advantageous in efficiently supplying needles in the proper posture.

(4) In the third selecting unit 52, the shape of the through hole 66, the recess 68, and the through hole 70 is not limited to the one illustrated in the drawings. In the case where the arrangement is designed to allow the needles N in the improper posture to fall into the through hole 66, as shown in the first embodiment, the through hole 66 may be formed into such a shape as to allow the needle in the proper posture to pass. In the case where the arrangement is designed to allow the needles N in the improper posture to fall on the side opposite to the side wall 64, as shown in the second embodiment, a hollow portion constituting the through hole and the recess may be formed into such a shape as to trap the end of the needle in the recess so as to lose the balance of the needle N moving forward in the improper posture.

In the latter case, the shape of the recess 68 and the through hole 70 is not limited to the above combination. Alternatively, the hollow portion may be, in its entirety, formed into a recess, or a through hole, as long as meeting the above requirements.

EXPLOITATION IN INDUSTRY

As mentioned above, the present invention is effectively applicable, in the field of producing such needles for surgical operations, to a needle supply device capable of properly selecting needles and supplying the same to a needle attached suture manufacturing apparatus.

We claim:

1. A needle supply device for accommodating curved needles and for supplying the needles in a certain posture to a predetermined position one by one, the needle supply device comprising:

a passage defining member including a needle storage portion in which the needles are accommodated, a needle discharge portion, and a needle path connecting the needle storage portion and the needle discharge portion;

needle conveyor means for forwarding the needle in the needle storage portion along the needle path to the needle discharge portion by vibrating the passage defining member;

select means in a passage form provided in the needle path for exclusively allowing the needle in the posture meeting a predetermined condition when the posture is maintained to pass; and said select means including a left/right selecting unit for exclusively allowing the needle with an intermediate portion curved in a predetermined direction to pass while maintaining the posture, said left/right selecting unit including a narrow path of a width smaller than the size of the needle in a direction perpendicularly crossing a needle transport direction, the width of the narrow path is set such that the center of gravity of the needle lies on the narrow path when the needle is transported with the intermediate portion thereof lying on the narrow path, and the center of gravity of the needle is offset from the narrow path when the needle is transported with the intermediate portion thereof deviated from the narrow path.

2. The needle supply device according to claim 1, wherein the narrow path is arranged at a level higher than the needle storage portion and a slope adjoining the narrow path is provided for guiding the needle falling off from the narrow path toward the needle storage portion.

3. A needle supply device for accommodating curved needles and for supplying the needles in a certain posture to a predetermined position one by one, the needle supply device comprising:

a passage defining member including a needle storage portion in which the needles are accommodated, a needle discharge portion and a needle path connecting the needle storage portion and the needle discharge portion;

needle conveyor means for forwarding the needle in the needle storage portion alone the needle path to the needle discharge portion by vibrating the passage defining member;

select means in a passage form provided in the needle path for exclusively allowing the needle in the posture meeting a predetermined condition when the posture is maintained to pass;

said select means including a left/right selecting unit for exclusively allowing the needle with an intermediate portion curved in a predetermined direction to pass while maintaining the posture, said left/right selecting unit including a through hole formed in a side wall constituting the needle path, the through hole having a size such that a point or an end of the needle can enter and the intermediate portion of the needle cannot enter, thereby ejecting the needle outside the needle path via the through hole when the point or the end of the needle enters the through hole, and allowing the needle to pass by the through hole when the needle does not enter the through hole.

4. A needle supply device for accommodating curved needles and for supplying the needles in a certain posture to a predetermined position one by one, the needle supply device comprising:

a passage defining member including a needle storage portion in which the needles are accommodated, a needle discharge portion, and a needle path connecting the needle storage portion and the needle discharge portion;

needle conveyor means for forwarding the needle in the needle storage portion along the needle path to the needle discharge portion by vibrating the passage defining member;

select means in a passage form provided in the needle path for exclusively allowing the needle in the posture meeting a predetermined condition when the posture is maintained to pass;

said select means including a left/right selecting unit for exclusively allowing the needle with an intermediate portion curved in a predetermined direction to pass while maintaining the posture, said left/right selecting unit including a partition wall for dividing the needle path along the direction perpendicularly crossing the needle transport direction into two regions, one region being an upstream passage communicating with the needle storage portion and the other region being a downstream passage communicating with the needle discharge portion, the partition wall being formed with a through hole having a size such that a point or an end of the needle can enter and the intermediate portion of the needle cannot enter, thereby allowing the needle to reach the downstream passage in a state that the direction of the needle is reversed by about 180 degrees when the point or the end of the needle enters the through hole, and allowing the needle to reach the downstream passage without changing the posture when the needle does not enter the through hole.

5. The needle supply device according to claim 4, wherein a side wall of the downstream passage is formed with a through hole of a size such that the point or the end of the needle can enter and the intermediate portion of the needle cannot enter, whereby ejecting the needle outside the needle path via the through hole when the point or the end of the needle passing the downstream passage enters the through hole, and allowing the needle to pass along the downstream passage when the needle does not enter the through hole.

6. A needle supply device for accommodating curved needles and for supplying the needles in a certain posture to a predetermined position one by one, the needle supply device comprising:

a passage defining member including a needle storage portion in which the needles are accommodated, a needle discharge portion, and a needle path connecting the needle storage portion and the needle discharge portion;

needle conveyor means for forwarding the needle in the needle storage portion along the needle path to the needle discharge portion by vibrating the passage defining member;

select means in a passage form provided in the needle path for exclusively allowing the needle in the posture meeting a predetermined condition when the posture is maintained to pass;

said select means including a front/rear selecting unit for allowing the needle to pass in a predetermined state that the point or the end of the needle is directed forward with respect to the needle transport direction, the needle path formed with the front/rear selecting unit including a bottom wall and a side wall upwardly extending from the bottom wall for supporting the needle in a tilted state, the side wall being formed with a hollow portion extending from an upper surface of the bottom wall or from a proximity thereof to a predetermined height level, and the height level and the configuration of the hollow portion being set so as to allow the needle to pass by the hollow portion with the point thereof in contact with an upper portion of the side wall above the hollow portion when the needle moves along the bottom wall in a state that the intermediate portion is in contact with the upper surface of the bottom wall and the point thereof is directed forward, and to allow the needle in a posture other than the above posture to be trapped in the hollow portion and ejected outside the needle path.

7. The needle supply device according to claim 6, wherein the hollow portion is a through hole formed on the side wall, and the needle with the point thereof coming into the through hole falls off from the bottom wall via the through hole.

8. The needle supply device according to claim 6, wherein the width of the bottom wall is set so as to offset the center of gravity of the needle from the bottom wall to the side away from the side wall when the needle enters the hollow portion.

9. A needle supply device for accommodating curved needles and for supplying the needles in a certain posture to a predetermined position one by one, the needle supply device comprising:

passage defining member including a needle storage portion in which the needles are accommodated, a needle discharge portion, and a needle path connecting the needle storage portion and the needle discharge portion;

needle conveyor means for forwarding the needle in the needle storage portion along the needle path to the needle discharge portion by vibrating the passage defining member;

select means in a passage form provided in the needle path for exclusively allowing the needle in the posture meeting a predetermined condition when the posture is maintained to pass;

needle detector means for detecting the needle discharged to the needle discharge portion; and conveyor control means for controlling the needle conveyor means to temporarily suspend a transport operation when the needle detector means detects the presence of the needle.

10. A needle supply device for accommodating curved needles and for supplying the needles in a certain posture to a predetermined position one by one, the needle supply device comprising:

a passage defining member including a needle storage portion in which the needles are accommodated, a needle discharge portion, and a needle path connecting the needle storage portion and the needle discharge portion;

needle conveyor means for forwarding the needle in the needle storage portion along the needle path to the needle discharge portion by vibrating the passage defining member; and select means in a passage form provided in the needle path for exclusively allowing the needle in the posture meeting a predetermined condition when the posture is maintained to pass, the select means including a left/right selecting unit having a narrow path having a width smaller than the size of the needle in a direction perpendicularly crossing a needle transport direction and an ordinary path having a width wider than the size of the needle in a direction perpendicularly crossing the needle transport direction for exclusively allowing the needle with an intermediate portion curved in a predetermined direction to pass while maintaining the posture, the width of the narrow path reducing from the width of the ordinary path in a stepwise manner.

11. A needle supply device for accommodating curved needles and for supplying the needles in a certain posture to a predetermined position one by one, the needle supply device comprising:

a passage defining member including a needle storage portion in which the needles are accommodated, a needle discharge portion, and a needle path connecting the needle storage portion and the needle discharge portion;

needle conveyor means for forwarding the needle in the needle storage portion along the needle path to the needle discharge portion by vibrating the needle defining member; and select means in a passage form provided in the needle path for exclusively allowing the needle in the posture meeting a predetermined condition when the posture is maintained to pass, the select means including a front/rear selecting unit a bottom wall and a side wall upwardly extending from the bottom wall for supporting the needle in a tilted state, the side wall being formed with a hollow portion, the hollow portion being set so as to allow the needle to pass by the hollow portion when the needle is in the posture corresponding to the predetermined condition and to trap the needle in the hollow portion when the needle is in a posture other than the predetermined condition.

12. A needle supply device for accommodating curved needles each including a point, an end and a curved intermediate portion extending therebetween, and for supplying the needles to a predetermined position in a desired posture one by one, the needle supply device comprising:

a passage defining member including a needle storage portion in which the needles are accommodated, a needle discharge portion, and a needle path connecting the needle storage portion and the needle discharge portion, the needles in the needle storage portion being conveyed along the needle path to the needle discharge portion in response to vibration applied to the passage defining member;

a first selecting unit disposed in said needle path comprising a narrow path and a slope arranged side by side in a direction orthogonal to a needle transport direction, the narrow path having a width smaller than a size of the needles in a direction perpendicularly crossing the needle transport direction and dimensioned such that when a needle meets a predetermined condition in which it is transported with the intermediate portion thereof lying on the narrow path, it is allowed to pass while a posture thereof is maintained, while other needles deviating from the predetermined condition travel down the slope in a direction away from the narrow path.

13. The needle supply device according to claim 12, wherein an end of the slope distant from the narrow path is connected with the needle storage portion such that needles which do not meet the predetermined condition travel down the slope and are returned to the needle storage portion.

14. A needle supply device for accommodating curved needles each including a point, an end and a curved intermediate portion extending therebetween, and for supplying the needles to a predetermined position in a desired posture one by one, the needle supply device comprising:

- a passage defining member including a needle storage portion in which the needles are accommodated, a needle discharge portion, and a needle path connecting the needle storage portion and the needle discharge portion, the needles in the needle storage portion being conveyed along the needle path to the needle discharge portion in response to vibration applied to the passage defining member;
- a second selecting unit provided in a position along said needle path in which an upstream passage of said needle path is disposed laterally offset in relation to the needle transport direction from a downstream passage of said needle path, said second selecting unit including a partition wall separating a segment of said upstream and downstream passages, said upstream and downstream passages being laterally communicative at a downstream boundary of said partition wall, a segment of said downstream passage being bounded by said partition wall and by a passage defining wall located laterally offset from said downstream passage, said partition wall including a through hole having a width selected such that the intermediate portion of the needles cannot enter the through hole and that the point and the end of the needles can each enter the through hole such that when a needle is in a predetermined posture in which it is oriented with the intermediate portion in contact with the partition wall the needle passes by the through hole and reaches the downstream passage without a change in the predetermined posture, and when in another posture other than the predetermined posture the needle enters the trough hole and into the segment of said downstream passage, said segment being configured such that such the direction of the needle in said another posture is reversed by about 180 degrees and into the predetermined posture in the downstream passage after entering the through hole.

15. The needle supply device according to claim 14, wherein said passage defining wall includes another through hole downstream from said though hole in said partition wall, said another through hole having a width selected such that the intermediate portion of the needles cannot enter the another through hole and that the point and the end of the needles can each enter the another through hole.

16. A needle supply device for accommodating curved needles each including a point, an end and a curved intermediate portion extending therebetween, and for supplying the needles to a predetermined position in a desired posture one by one, the needle supply device comprising:

- a passage defining member including a needle storage portion in which the needles are accommodated, a needle discharge portion, and a needle path connecting the needle storage portion and the needle discharge portion, the needles in the needle storage portion being conveyed along the needle path to the needle discharge portion in response to vibration applied to the passage defining member;
- a third selecting unit provided in the needle path including a bottom wall and a side wall upwardly extending from the bottom wall for supporting the needle in a tilted state, the side wall including a hollow portion, the hollow portion being configured to allow a needle to pass by the aperture with a point of the needle in contact with an upper portion of the side wall above the hollow portion when the needle moves along the bottom wall in a desired state in which the intermediate portion is in contact with an upper surface of the bottom wall and the point thereof is directed forward, and to cause the needle to be trapped by the hollow portion when the needle is in other than the desired state and a point thereof is not in contact with the upper portion of the side wall above the hollow portion.

17. The needle supply device according to claim 16, wherein a widthwise dimension of said bottom wall is substantially coincident with a diameter of the needles, whereby an overlapping of plural needles is prevented.

18. The needle supply device according to claim 16, wherein said hollow portion is a through hole bounded by a straight upright edge extending from the bottom wall, a curved edge extending from said bottom wall at a downstream side of the upright edge and a horizontal edge connecting upper ends of the upright edge and the curved edge.

19. The needle supply device according to claim 16, wherein said hollow portion includes a recess and a through hole formed continuously with the recess at an upper end of the recess.

20. The needle supply device according to claim 19, wherein a depth of said recess increases approaching said upper end.

* * * * *